United States Patent
Liu

(10) Patent No.: US 9,036,783 B2
(45) Date of Patent: May 19, 2015

(54) GAIN CALIBRATION TECHNIQUE FOR DIGITAL IMAGING SYSTEMS

(75) Inventor: James Zhengshe Liu, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 325 days.

(21) Appl. No.: 13/568,912

(22) Filed: Aug. 7, 2012

(65) Prior Publication Data

US 2014/0044232 A1 Feb. 13, 2014

(51) Int. Cl.
*H05G 1/64* (2006.01)
*H04N 5/32* (2006.01)
*G01N 23/04* (2006.01)

(52) U.S. Cl.
CPC . *H04N 5/32* (2013.01); *G01N 23/04* (2013.01)

(58) Field of Classification Search
CPC ........ G01N 23/04; A61B 6/483; A61B 6/032; H04N 5/32
USPC .......... 378/6, 62, 98.4, 98.11, 98.12; 382/128–131
See application file for complete search history.

(56) References Cited

U.S. PATENT DOCUMENTS

| | | |
|---|---|---|
| 2008/0075349 A1 | 3/2008 | Ritter et al. |
| 2010/0020933 A1* | 1/2010 | Topfer et al. ............... 378/98.11 |
| 2010/0054400 A1* | 3/2010 | Ren et al. ......................... 378/37 |
| 2010/0183124 A1 | 7/2010 | Liu et al. |
| 2012/0019669 A1* | 1/2012 | Bai et al. ....................... 348/187 |

OTHER PUBLICATIONS

International Search Report and Written Opinion for PCT/US2013/053975, mail date Jan. 14, 2014, 9 pages.

* cited by examiner

*Primary Examiner* — Courtney Thomas
(74) *Attorney, Agent, or Firm* — Fletcher Yoder, P.C.

(57) ABSTRACT

A computer-implemented method for gain calibration is provided. The method includes sorting the calibration data of each pixel location from the offset-corrected X-ray image data into a sequence. The method also includes removing part of the calibration data from one end or both ends of the respective sequence for each pixel location. The method further includes averaging the calibration data remaining within each respective sequence to obtain an average pixel value for each pixel location. The method yet further includes generating a gain map based on the average pixel value for each pixel location.

25 Claims, 4 Drawing Sheets

GAIN CALIBRATION TECHNIQUE FOR DIGITAL IMAGING SYSTEMS

BACKGROUND

A number of radiological and fluoroscopic imaging systems of various designs are known and are presently in use. Such systems generally are based upon generation of X-rays that are directed toward a subject of interest. The X-rays traverse the subject and impact a digital detector or an image intensifier. In medical contexts, for example, such systems may be used to visualize internal bones, tissues, and organs, and diagnose and treat patient ailments. In other contexts, parts, baggage, parcels, and other subjects may be imaged to assess their contents. In addition, radiological and fluoroscopic imaging systems may be used to identify the structural integrity of objects and for other purposes.

Increasingly, such X-ray systems use digital circuitry, such as solid-state detectors, for detecting the X-rays, which are attenuated, scattered or absorbed by the intervening structures of the subject. It will be appreciated that raw image data acquired via such X-ray systems may include a number of artifacts or other undesirable elements that may, if left uncorrected, result in visual artifacts in a reconstructed image based on the raw image data. In turn, these visual artifacts may negatively impact the ability of a user or computer to discern finer details in the image. For example, non-uniformity of various aspects of the X-ray system, such as the X-ray beam, diodes and/or data channels of a digital detector, and the like, may result in gain variation in the acquired raw image data. While certain approaches for performing gain calibration and correcting image data for such gain variation may be known, these approaches are not applicable to certain types of detectors such as complementary metal-oxide-semiconductor (CMOS) based detectors due to the presence of impulse-type noise generated by direct X-ray hits on the light imager. There is a need, therefore, for improved approaches to gain calibration for digital imaging systems that account for impulse-type noise.

BRIEF DESCRIPTION

In accordance with a first embodiment, a computer-implemented method for gain calibration is provided. The method includes sorting calibration data for each pixel location from offset-corrected X-ray calibration image data into a sequence. The method also includes removing part of the calibration data from one end or both ends of the sequence for each pixel location. The method further includes averaging the calibration data remaining within each respective sequence to obtain an average pixel value for each pixel location. The method yet further includes generating a gain map based on the average pixel value for each pixel location.

In accordance with a second embodiment, a computer-implemented method is provided. The method uses a digital X-ray system to execute a gain calibration process via the digital X-ray system. The gain calibration process includes sorting calibration data for each pixel location from offset-corrected X-ray image data into a sequence. The gain calibration process also includes removing part of the calibration data from one end or both ends of the sequence for each pixel location. The gain calibration process further includes averaging the calibration data remaining within each respective sequence to obtain an average pixel value for each pixel location. The gain calibration process yet further includes generating a gain map based on the average pixel value for each pixel location.

In accordance with a third embodiment, an imaging system is provided. The imaging system includes a radiation source, a digital detector configured to generate image data, and control circuitry configured to acquire the image data from the digital detector. The imaging system also includes processing circuitry configured to apply gain correction to the image data via a gain map, wherein the processing circuitry is configured to generate the gain map by executing code to perform the following acts. The acts include sorting calibration data for each pixel location from offset-corrected image data into a sequence and removing part of the calibration data from a respective sequence for each pixel location. The acts also include averaging the calibration data remaining within each respective sequence to obtain an average pixel value for each pixel location. The acts further include generating the gain map based on the average pixel value for each pixel location.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

The present disclosure provides for methods and systems to perform gain calibration for radiographic detectors where impulse-type noise (i.e., noise generated by direct X-ray hits on the light imager of the detector) is present. For example, detectors such as complementary metal-oxide-semiconductor (CMOS) based detectors may experience impulse-type noise. However, the techniques discussed below may be applied to other types of detectors (e.g., amorphous silicon based detectors). The techniques discussed below remove part of the calibration data from the image data that may include impulse-type noise prior to generating a gain map. In addition, the techniques discussed below may reduce Gaussian noise (i.e., electronic noise) present in the remaining calibration data prior to generating the gain map. The techniques described below may be utilized in a variety of radiographic imaging systems, such as computed tomography (CT) systems, fluoroscopic imaging systems, mammography systems, tomosynthesis imaging systems, conventional radiographic imaging systems, and so forth. However, it should be appreciated that the described techniques may also be used in non-medical contexts (such as security and screening systems and non-destructive detection systems).

Figure 1:
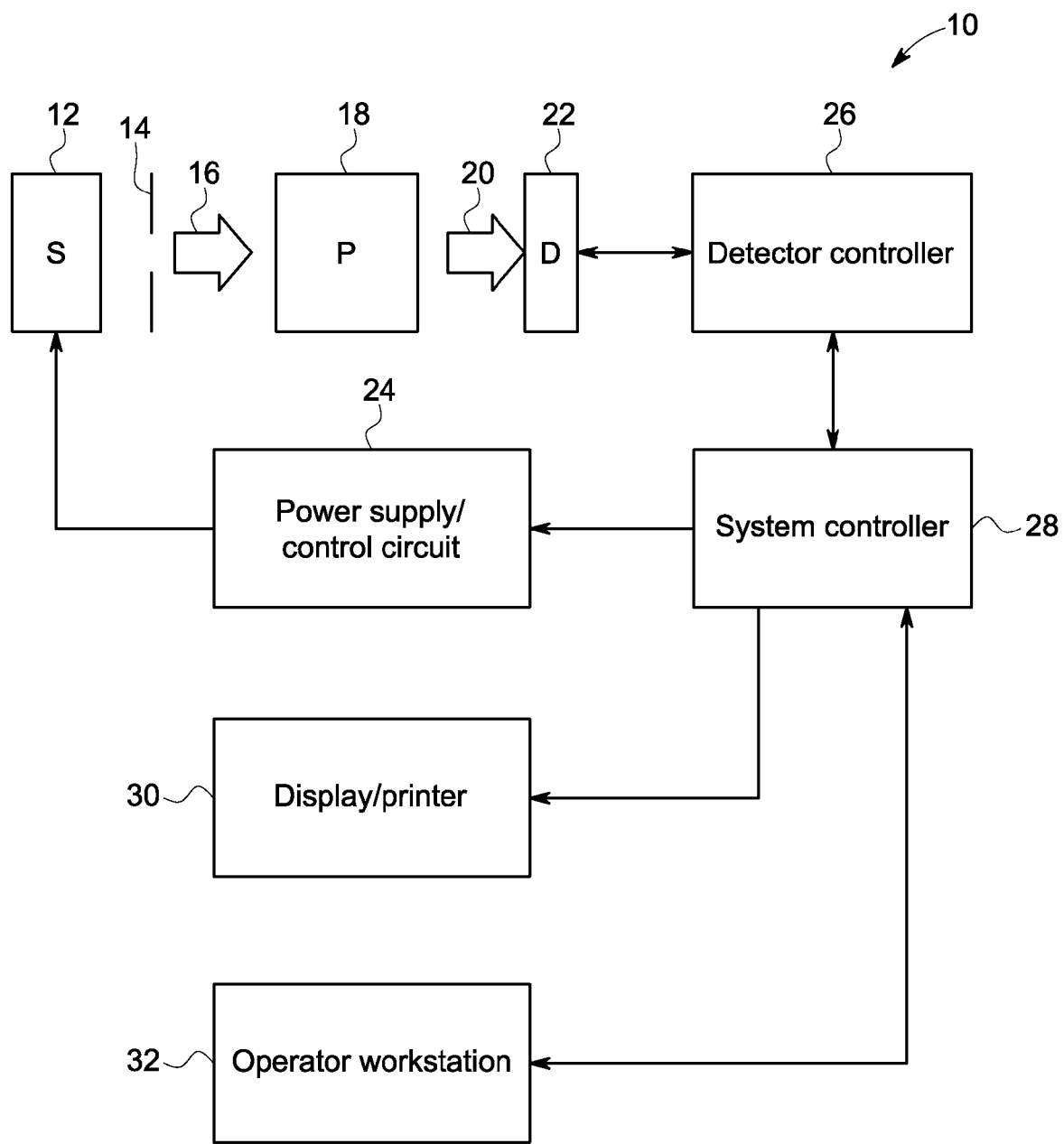
FIG. 1 is a diagrammatical overview of a digital X-ray imaging system in which the present technique may be utilized.

Turning now to the drawings, FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. The imaging system 10 may be a stationary system disposed in a fixed X-ray imaging room or a mobile X-ray system. In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. The detector 22 may be portable or permanently mounted to the system 10. In certain embodiments, the detector 22 may convert the X-ray photons incident on its surface to lower energy photons, and subsequently to electric signals, which are acquired and processed to reconstruct an image of the features within the subject. In other embodiments, such as in a direct conversion implementation, the incident radiation itself may be measured without an intermediary conversion process.

Source 12 is controlled by a power supply/control circuit 24 which furnishes both power and control signals for examination sequences. Moreover, detector 22 is coupled to a detector controller 26 which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer; and associated manufactures, such as optical memory devices, magnetic memory devices, or solid-state memory devices, for storing programs and routines executed by a processor of the computer to carry out various functionalities (e.g., gain calibration and gain correction), as well as for storing configuration parameters and image data; interface protocols; and so forth. In one embodiment, a general or special purpose computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
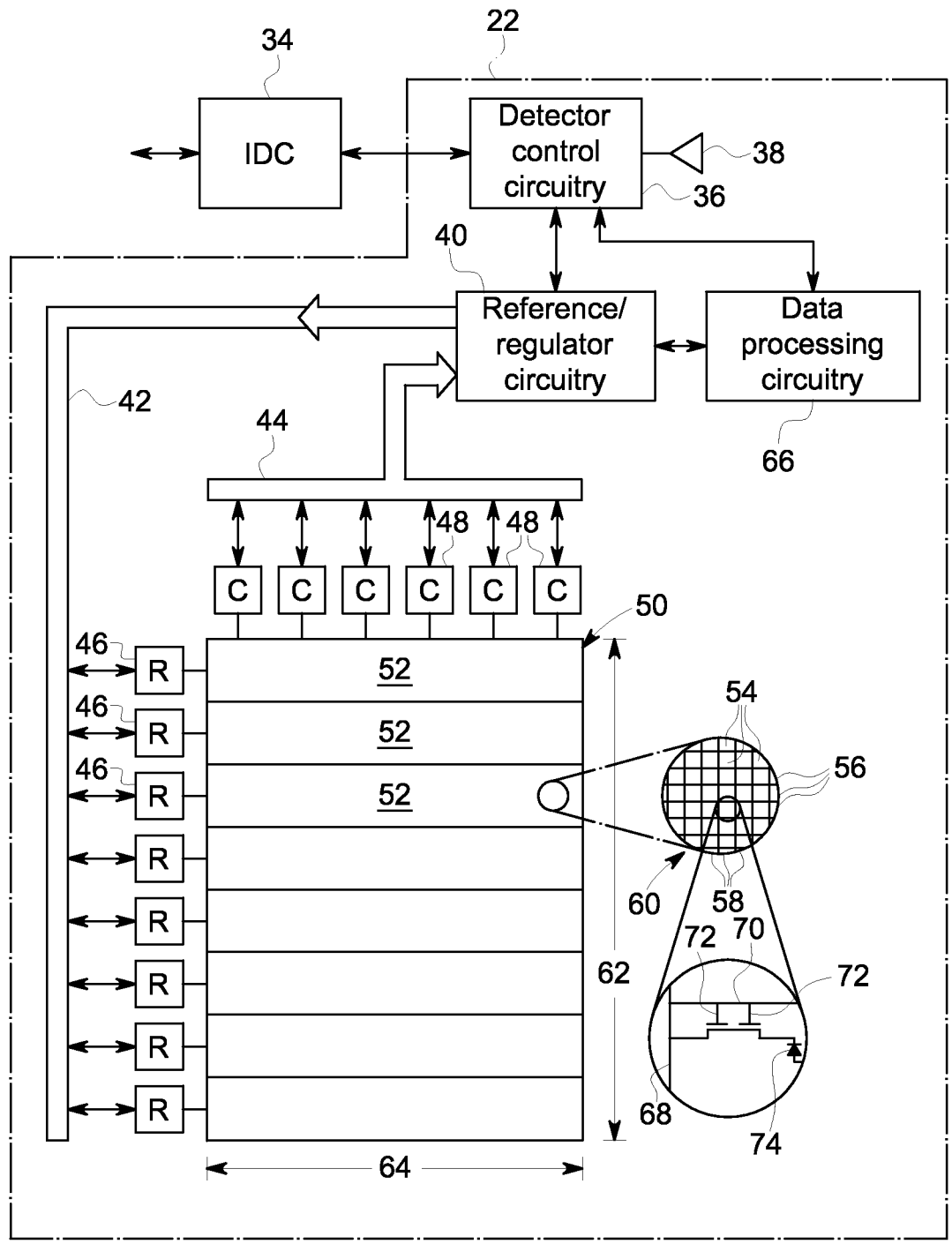
FIG. 2 is a diagrammatical representation of the functional circuitry in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. In one implementation, IDC 34 is coupled via two-way fiberoptic conductors to detector control circuitry 36 within detector 22. In certain presently contemplated embodiments, other communications systems and technologies may be used, such as Ethernet communications protocols, and wireless communications devices and protocols. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column electronics used to acquire image data during data acquisition phases of operation of the system. Circuitry 36 therefore transmits power and control signals to reference/regulator circuitry 40, and receives digital image pixel data from circuitry 40.

In a present embodiment, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions of the detector surface. In certain presently contemplated embodiments, the X-ray photons may be directly converted to electrical signals. Readout electronics convert the resulting analog signals to digital values that can be processed, stored, and displayed, such as in a display 30 or a workstation 32 following reconstruction of the image. In a present form, the array of photodetectors is formed of silicon CMOS. The array elements are organized in rows and columns, with each element consisting of a photodiode and complementary and symmetrical pairs of p-type and metal oxide semiconductor field effect transistors (MOFSET). The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual data channel of the readout electronics.

In the particular embodiment illustrated in FIG. 2, by way of example, a row bus 42 includes a plurality of conductors for enabling readout from various rows of the detector 22, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50, which may be subdivided into a plurality of sections 52. Each section 52 is coupled to one of the row drivers 46, and includes a number of rows. Similarly, each column driver 48 is coupled to a series of columns. The photodiode and transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode (or data line) 68 crosses a row electrode (or scan line) 70. As mentioned above, a couple of MOFSETS 72 is provided at each crossing location for each pixel, as is a photodiode 74. As each row is enabled by row drivers 46, signals from each photodiode 74 may be accessed via readout electronics 48, and converted to digital signals for subsequent processing and image reconstruction. Thus, an entire row of pixels in the array is controlled simultaneously when the scan line 70 attached to the gates of all the transistors of pixels on that row is activated. Consequently, each of the pixels in that particular row is connected to a data line 68, through a switch, which is used by the readout electronics to restore the charge to the photodiode 74 and measure an amount of charge depletion resulting from irradiation.

It should be noted that in certain systems, as the charge is restored to all the pixels in a row simultaneously by each of the associated dedicated readout channels, the readout electronics is converting the measurements from the previous row from an analog voltage to a digital value. Furthermore, the readout electronics may transfer the digital values from rows previous to the acquisition subsystem, which will perform some processing prior to displaying a diagnostic image on a monitor or writing it to film. In at least some embodiments, the digital detector 22 may include data processing circuitry 66 configured to perform some local processing of the data acquired via the detector panel 50 within the digital detector itself. For instance, as discussed in greater detail below, the digital detector 22 may be configured to perform gain calibration and gain correction (e.g., to reduce impulse-type noise and Gaussian noise) to the acquired data independent of a host processing system, such as the system controller 28. Additionally, in one embodiment, the digital detector 22 may perform such calibration and apply such correction to the acquired data before outputting the data to other components of the system 10.

The circuitry used to enable the rows may be referred to in a present context as row enable or MOFSET circuitry based upon the use of complementary and symmetrical pairs of p-type and metal oxide semiconductor field effect transistors for such enablement (row driving). The MOFSETs associated with the row enable circuitry described above are placed in an "on" or conducting state for enabling the rows, and are turned "off" or placed in a non-conducting state when the rows are not enabled for readout. Despite such language, it should be noted that the particular circuit components used for the row drivers and column readout electronics may vary, and the present invention is not limited to the use of MOFSETs or any particular circuit components.

Figure 3:
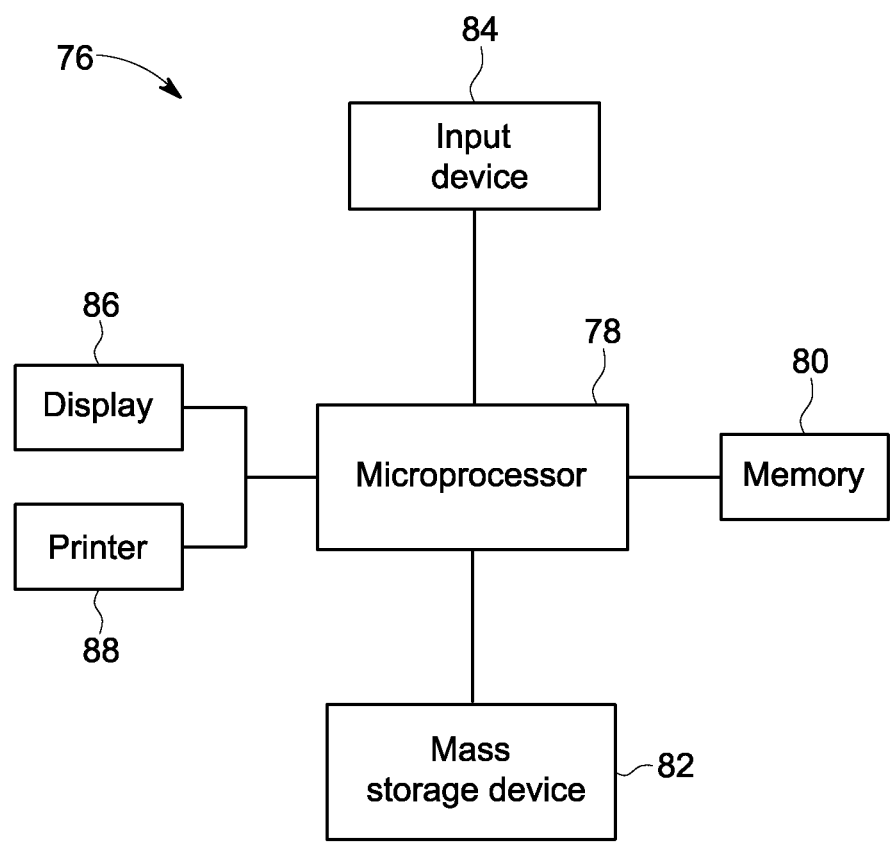
FIG. 3 is a block diagram of a processor-based device or system that may be configured to implement functionality described herein in accordance with one embodiment.

Various functionality, including image data gain correction and calibration of the detector 22 described herein, may be performed by, or in conjunction with, a processor-based system 76, which is generally depicted in FIG. 3 in accordance with one embodiment. For example, the various controllers and circuitry discussed herein may include, or be partially or entirely embodied in, a processor-based system, such as that presently illustrated. The processor-based system 76 may be a general-purpose computer, such as a personal computer, configured to run a variety of software, including software implementing all or part of the functionality described herein. Alternatively, in other embodiments, the processor-based system 76 may include, among other things, a distributed computing system, or an application-specific computer or workstation configured to implement all or part of the presently described functionality based on specialized software and/or hardware provided as part of the system. Further, the processor-based system 76 may include either a single processor or a plurality of processors to facilitate implementation of the presently disclosed functionality.

In one embodiment, the exemplary processor-based system 76 includes a microcontroller or microprocessor 78, such as a central processing unit (CPU), which executes various routines and processing functions of the system 76. For example, the microprocessor 78 may execute various operating system instructions, as well as software routines configured to effect certain processes, stored in or provided by a manufacture including one or more computer readable-media (at least collectively storing the software routines), such as a memory 80 (e.g., a random access memory (RAM) of a personal computer) or one or more mass storage devices 82 (e.g., an internal or external hard drive, a solid-state storage device, a CD-ROM, a DVD, or another storage device). In addition, the microprocessor 78 processes data provided as inputs for various routines or software programs, such as data provided as part of the present subject matter described herein in computer-based implementations.

Such data may be stored in, or provided by, the memory 80 or mass storage device 82. Alternatively, such data may be provided to the microprocessor 78 via one or more input devices 84. The input devices 84 may include manual input devices, such as a keyboard, a mouse, or the like. In addition, the input devices 84 may include a network device, such as a wired or wireless Ethernet card, a wireless network adapter, or any of various ports or devices configured to facilitate communication with other devices via any suitable communications network, such as a local area network or the Internet. Through such a network device, the system 76 may exchange data and communicate with other networked electronic systems, whether proximate to or remote from the system 76.

Results generated by the microprocessor 78, such as the results obtained by processing data in accordance with one or more stored routines, may be provided to an operator via one or more output devices, such as a display 86 and/or a printer 88. Based on the displayed or printed output, an operator may request additional or alternative processing or provide additional or alternative data, such as via the input device 84. Communication between the various components of the processor-based system 76 may typically be accomplished via a chipset and one or more busses or interconnects which electrically connect the components of the system 76. In one embodiment, the exemplary processor-based system 76 can be configured to, among other things, receive image data, generate a gain map or gain correction map, apply gain correction to the image data via one or more gain correction maps, and output the corrected image data.

Figure 4:
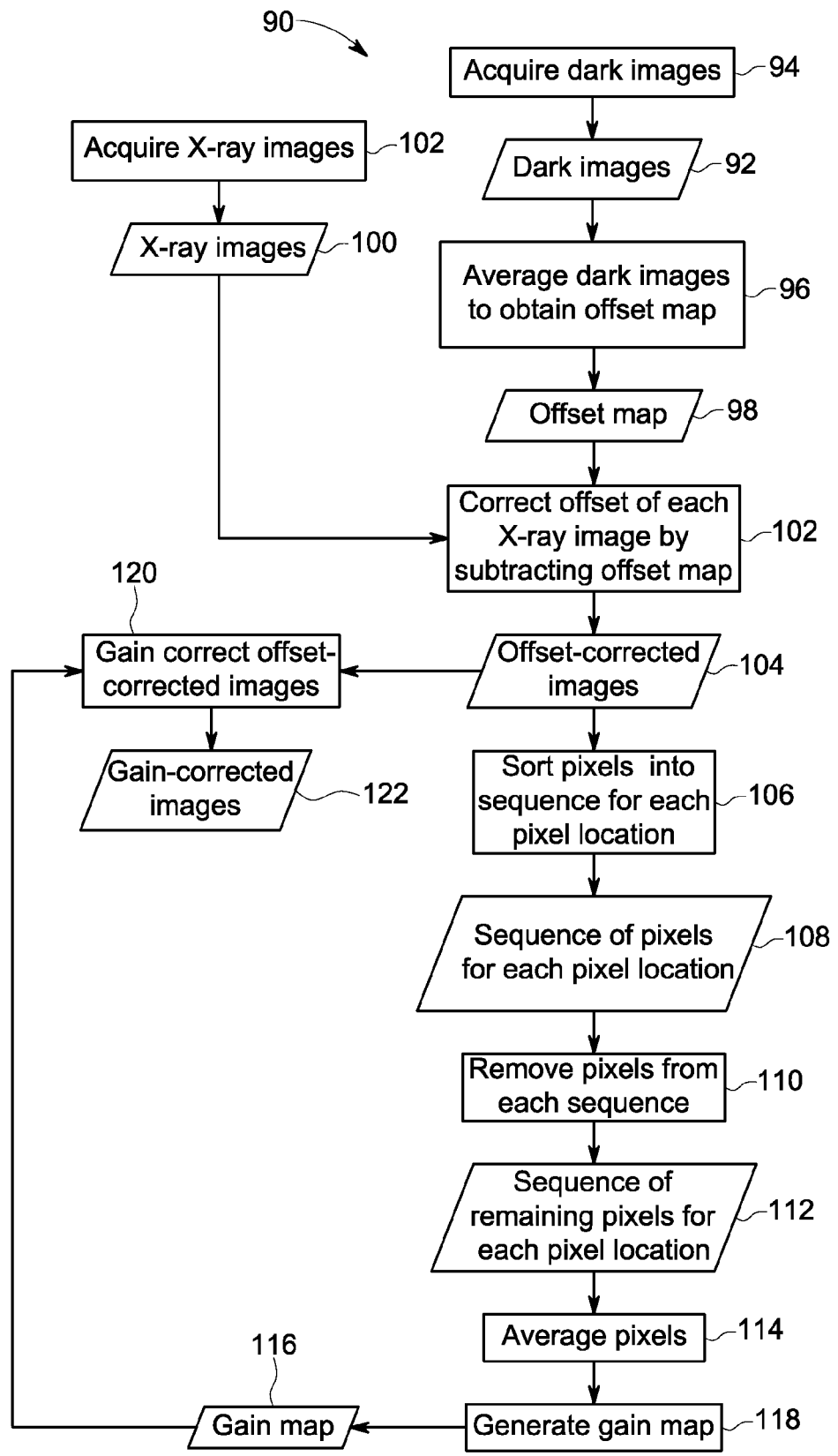
FIG. 4 is a flowchart of a process for operating a digital X-ray imaging system in accordance with one embodiment.

FIG. 4 illustrates a method 90 for operating the digital X-ray imaging system 10 (e.g., acquiring image data, gain calibration, and gain correction). The followings acts of method 90 may be performed by various control circuitry and processing circuitry of the system 10 (e.g., by the detector 22 and/or by components of the system 10 external to the detector 22). The method 90 includes acquiring dark images or offset images 92 (i.e., images acquired when the detector 22 is not exposed to radiation from the source 12) (block 94) represented by $$O^{(m)} \triangleq \{o_{i,j}^{(m)}\}.$$

O represents the offset images, m=0, 1, ... M−1 with M being the number of dark images 92 available, and i=0, 1, ... I−1 and j=0, 1, ... J−1 with/and J, respectively, being the number of rows and columns of the detector 22. The dark images 92 only include the Gaussian type of electric noise. The method 90 includes averaging the M available dark images 92 (block 96) to obtain an offset map 98, $\hat{O}$, with minimum noise. The averaging of the dark images 92 to obtain the offset map 98 is described by the following:

$$\hat{O} \triangleq \{\hat{o}_{i,j}\} = \frac{1}{M} \sum_{m=0}^{M-1} o_{i,j}^{\{m\}}. \quad (1)$$

The method 90 also includes acquiring X-ray images or X-ray image data 100 (block 102) represented by $$X^{\{n\}} \triangleq \{x_{i,j}^{\{n\}}\},$$

where n=0, 1, ... N−1 with N being the X-ray images available. After obtaining the X-ray images 100, the method 90 includes correcting the N X-ray images 100 by subtracting the obtained offset map 98 (block 102) from each of the N X-ray images 100

$$\hat{X}^{\{n\}} \triangleq \{\hat{x}_{i,j}^{\{n\}}\} = X^{\{n\}} - \hat{O} = \{x_{i,j}^{\{n\}} - \hat{o}_{i,j}\}, \quad (2)$$

where $\hat{X}^{\{n\}}$ represents an offset-corrected image 104 for each respective X-ray image 100.

The offset-corrected images 104 may include a Gaussian-type of electric noise and/or impulse-type noise due to direct X-ray hits on the imager of the detector 22. To minimize the impulse-type noise within the offset-corrected images 104, the method 90 includes sorting pixels (block 106), $\{\hat{x}_{i,j}^{\{n\}}, n=0, 1, \ldots, N-1\}$, from the N offset-corrected images 104 based on their pixels values (e.g., calibration data) for each pixel location (i, j) to generate a sequence 108 $\{\ldots, \hat{s}_{i,j}^{\{-L\}}, \ldots, \hat{s}_{i,j}^{\{-1\}}, \hat{s}_{i,j}^{\{0\}}, \hat{s}_{i,j}^{\{1\}}, \ldots, \hat{s}_{i,j}^{\{L\}}\}$, where $\hat{s}_{i,j}^{\{0\}}$ is the median pixel value of the sequence 108 for each respective pixel location and L is an experimentally determined parameter interceded to balance the performance between the impulse-type and Gaussian type of noises. The generated sequence 108 (e.g., of calibration data) for each pixel location may be an ascending sequence or a descending sequence.

Upon generating the sequences 108 for each pixel location (block 106), the method 90 includes removing values (e.g., calibration data) that may contain the impulse-type of noise from the left and/or right hand sides (i.e., relative to the median pixel value) (block 110) of each sequence 108 to generate a sequence of remaining pixels 112 (i.e., remaining calibration data or pixel values) for each pixel location. The calibration data may be removed from a beginning of a descending sequence, an end of an ascending sequence, or both from the beginning and end of the sequence 108. The method 90 then includes averaging the pixel values (e.g., calibration data) of the 2L+1 middle pixels (i.e., remaining pixels) of each respective sequence 112 (block 114) to obtain an average pixel value for each pixel location and to reduce the electronic noise (e.g., Gaussian noise) as described in the following:

$$\hat{S} \triangleq \{\hat{s}_{i,j}\} = \frac{1}{2L+1}\left[s_{i,j}^{\{0\}} + \sum_{l=1}^{L}(\hat{s}_{i,j}^{\{-l\}} + \hat{s}_{i,j}^{\{l\}})\right], \quad (3)$$

where $\{\hat{s}_{i,j}\}$ represents the average pixel value for the middle pixels or the remaining pixels of the respective sequence 112 for each pixel location.

The method 90 further includes generating a gain map 116 (block 118) from the average pixels values. The gain map 116 is obtained by $$\hat{G} \triangleq \{\hat{g}_{i,j}\} = \frac{\text{median}\{\hat{s}_{i,j}\}}{\hat{s}_{i,j}}, \quad (4)$$

where median$\{\hat{s}_{i,j}\}$ is the median pixel value over the I×J pixels of $\{\hat{s}_{i,j}\}$. In particular, the gain map 116 is obtained for each pixel location by dividing the median pixel value over the I×J pixels by the average pixel value for the respective pixel location. Upon obtaining the gain map 116 (block 118), the method 90 includes gain correcting the offset-corrected images 104 (block 120) to generate gain-corrected images or image data 122.

Technical effects of the disclosed embodiments include providing methods and systems to perform gain calibration and correction for radiographic detectors 22 where impulse-type noise is present. In particular, the disclosed embodiments include sorting pixels from offset-corrected image data for each pixel location into a sequence based on a value (e.g., calibration data) of each pixel and removing those values from the sequence that may include impulse-type noise. The disclosed embodiments further include averaging the values for the remaining data within the sequence for each pixel location to minimize Gaussian-type noise and to obtain the gain map. Upon obtaining the gain map, the offset-corrected images may be gain-corrected to generate gain-corrected images to improve the image quality of the images.

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for gain calibration comprising:
   sorting a plurality of pixel values obtained from a plurality of offset-corrected X-ray images at a given pixel location into a sequence based on pixel value for each pixel location;
   removing one or more pixel values on one end or both ends of the sequence for each pixel location;
   averaging the remaining pixel values within each respective sequence to obtain an average pixel value for each pixel location; and
   generating a gain map based on the average pixel value for each pixel location.

2. The method of claim 1, wherein the sequence comprises an ascending sequence or descending sequence.

3. The method of claim 1, wherein removing the one or more pixel values comprises removing the one or more pixel values from the beginning of a descending sequence, removing the one or more pixel values from the end of an ascending sequence, or removing the one or more pixel values from both the beginning and the end of the sequence.

4. The method of claim 1, comprising generating the plurality of offset-corrected X-ray images.

5. The method of claim 4, wherein generating the plurality of offset-corrected X-ray images comprises:
acquiring a plurality of dark images from a digital image detector of an X-ray system;
averaging the plurality of dark images to obtain an offset map;
acquiring a plurality of X-ray images from the digital image detector; and
subtracting the offset map from each X-ray image of the plurality of X-ray images to generate the offset-corrected X-ray images.

6. The method of claim 5, wherein the digital detector comprises a complementary metal-oxide-semiconductor (CMOS) based detector.

7. The method of claim 1, wherein the gain map is generated for each pixel location by dividing a median pixel value obtained from the average pixel values of all of the pixel locations by the average pixel value of each respective pixel location.

8. The method of claim 1, comprising correcting at least one of the plurality of offset-corrected X-ray images with the gain map to generate at least one corrected X-ray image.

9. A computer-implemented method comprising:
using a digital X-ray system to:
execute a gain calibration process via the digital X-ray system comprising:
sorting a plurality of pixel values obtained from a plurality of offset-corrected X-ray images at a given pixel location into a sequence based on pixel value for each pixel location;
removing one or more pixel values from one end or both ends of the sequence for each pixel location;
averaging the remaining pixel values within each respective sequence to obtain an average pixel value for each pixel location; and
generating a gain map based on the average pixel value for each pixel location.

10. The method of claim 9, comprising using the digital X-ray system to execute a first imaging process via the digital X-ray system, the first imaging process comprising:
acquiring a plurality of dark images from a digital image detector of the digital X-ray system; and
averaging the plurality of dark images to obtain an offset map.

11. The method of claim 10, wherein the first imaging process further comprises:
acquiring a plurality of X-ray-images from the digital image detector; and
subtracting the offset map from each X-ray image of the plurality of X-ray images data to generate the plurality of offset-corrected X-ray images.

12. The method of claim 9, wherein the digital image detector comprises a complementary metal-oxide-semiconductor (CMOS) based detector.

13. The method of claim 9, wherein the sequence comprises an ascending sequence or descending sequence.

14. The method of claim 9, wherein removing part of the calibration data comprises removing the one or more pixel values from the beginning of a descending sequence, removing the one or more pixel values from the end of an ascending sequence, or removing the one or more pixel values from both the beginning and the end of the sequence.

15. The method of claim 9, wherein the gain map is generated for each pixel location by dividing a median pixel value obtained from the average pixel values of all of the pixel locations by the average pixel value of each respective pixel location.

16. The method of claim 9, comprising using the digital X-ray system to execute a second imaging process via the digital X-ray system, wherein the second imaging process comprises correcting at least one of the plurality of offset-corrected X-ray images with the gain map to generate at least one gain-corrected X-ray image.

17. An imaging system comprising:
a radiation source;
a digital detector configured to generate image data;
control circuitry configured to acquire the image data from the digital detector; and
processing circuitry configured to apply gain correction to the image data via a gain map, wherein the processing circuitry is configured to generate the gain map by executing code to perform the acts of:
sorting a plurality of pixel values obtained from a plurality of offset-corrected X-ray images at a given pixel location into a sequence based on pixel value for each pixel location;
removing one or more pixel values from a respective sequence for each pixel location;
averaging the remaining pixel values within each respective sequence to obtain an average pixel value for each pixel location; and
generating the gain map based on the average pixel value for each pixel location.

18. The imaging system of claim 17, wherein the control circuitry is configured to acquire a plurality of dark images from the digital detector, and the processing circuitry is configured to average the plurality of dark images to generate an offset map and to subtract the offset map from each X-ray image of the plurality of X-ray images to generate the plurality of offset-corrected images.

19. The imaging system of claim 17, wherein the digital detector comprises a complementary metal-oxide-semiconductor (CMOS) based detector.

20. The imaging system of claim 17, wherein the sequence comprises an ascending sequence or descending sequence.

21. The imaging system of claim 17, wherein removing part the one or more pixel values comprises removing the one or more pixel values from the beginning of a descending sequence, removing the one or more pixel values from the end of an ascending sequence, or removing the one or more pixel values from both the beginning and the end of a sequence.

22. The imaging system of claim 17, wherein generating the gain map for each pixel location comprises dividing a median pixel value obtained from the average pixel values of all of the pixel locations by the average pixel value of each respective pixel location.

23. The imaging system of claim 22, wherein the processing circuitry is configured to execute code to correct at least one of the plurality of offset-corrected X-ray images with the gain map to generate at least one gain-corrected X-ray image.

24. The imaging system of claim 17, wherein the digital detector comprises the memory device and at least a portion of the processing circuitry.

25. The imaging system of claim 17, wherein the digital detector comprises the memory device and at least a portion of the processing circuitry.

* * * * *